United States Patent
Barlos

(10) Patent No.: US 10,183,966 B2
(45) Date of Patent: Jan. 22, 2019

(54) SOLID PHASE PEPTIDE SYNTHESIS VIA SIDE CHAIN ATTACHMENT

(71) Applicant: CHEMICAL & BIOPHARMACEUTICAL LABORATORIES OF PATRAS S.A., Patras (GR)

(72) Inventor: Kleomenis K. Barlos, Patras (GR)

(73) Assignee: CHEMICAL & BIOPHARMACEUTICAL LABORATORIES OF PATRAS S.A., Patras (GR)

(*) Notice: Subject to any disclaimer, the term of this patent is extended or adjusted under 35 U.S.C. 154(b) by 127 days.

(21) Appl. No.: 15/182,213

(22) Filed: Jun. 14, 2016

(65) Prior Publication Data
US 2016/0362445 A1 Dec. 15, 2016

Related U.S. Application Data

(62) Division of application No. 13/772,793, filed on Feb. 21, 2013, now Pat. No. 9,388,212.

(51) Int. Cl.
| | |
|---|---|
| *A61K 38/00* | (2006.01) |
| *C07K 9/00* | (2006.01) |
| *C07K 1/04* | (2006.01) |
| *C07K 14/575* | (2006.01) |
| *C07K 14/585* | (2006.01) |
| *C07K 14/815* | (2006.01) |
| *C07K 7/06* | (2006.01) |
| *C07K 1/06* | (2006.01) |
| *C07K 7/08* | (2006.01) |
| *C07K 7/64* | (2006.01) |
| *C07K 14/605* | (2006.01) |
| *C07K 14/62* | (2006.01) |

(52) U.S. Cl.
CPC .......... *C07K 1/042* (2013.01); *C07K 1/061* (2013.01); *C07K 1/062* (2013.01); *C07K 7/06* (2013.01); *C07K 7/08* (2013.01); *C07K 7/64* (2013.01); *C07K 14/575* (2013.01); *C07K 14/585* (2013.01); *C07K 14/605* (2013.01); *C07K 14/62* (2013.01); *C07K 14/815* (2013.01)

(58) Field of Classification Search
None
See application file for complete search history.

(56) References Cited

U.S. PATENT DOCUMENTS

| | | | |
|---|---|---|---|
| 4,254,023 A | 3/1981 | Stewart et al. | |
| 7,939,629 B2 * | 5/2011 | Droz ................ | C07K 14/815 530/300 |
| 2004/0249121 A1 | 12/2004 | Tovi et al. | |

FOREIGN PATENT DOCUMENTS

| | | |
|---|---|---|
| EP | 0 606 816 A1 | 7/1994 |
| EP | 2 270 025 A1 | 1/2011 |
| JP | H06-234793 A | 8/1994 |
| JP | 2005-501058 A | 1/2005 |
| JP | 2007-513192 A | 5/2007 |
| JP | 2008-517018 A | 5/2008 |
| WO | 2003/011892 A2 | 2/2003 |
| WO | 2005/087794 A1 | 9/2005 |
| WO | 2006/041945 A2 | 4/2006 |
| WO | 2006/045503 A1 | 5/2006 |

OTHER PUBLICATIONS

Maruyama et al. (1976) "Solid Phase Peptide Synthesis by Oxidation-Reduction Condensation. Synthesis of Adrenocorticotropin(1-24) by Chain Elongation at the Carboxyl End on Solid Support," Bulletin of the Chemical Society of Japan. 49(8):2259-2267.
Alsina et al. (1997) "Active Carbonate Resins for Solid-phase synthesis through the anchoring of a hydroxyl function. Synthesis of cyclic and alcohol peptides," Tetrahedron Letters. 38(5):883-886.
Alsina et al. (2003) "Solid-phase synthesis of C-terminal modified peptides," Peptide Science. 71(4):454-477.
Bernhardt et al. (1997) "The solid-phase synthesis of side-chain-phophorylated peptide-4-nitroanilidies," J Peptide Res. 50:143-152.
Cabrele et al. (1999) "Amino Acid Side Chain attachment approach and its application to the synthesis of trysoine-containing cyclic peptides," J. Org. Chem. 64:4353-4361.
Chan et al. (2000) Fmoc Solid Phase Peptide Synthesis: A practical approach. Series 222. Oxford University Press. pp. 223-227.
Graham et al. (2002) "A general method for functionalising both the C- and N-terminals of Tyr 3-octreotate," Tetrahedron Letters. 43(29):5021-5024.
Mergler et al. (1999) "Solid phase synthesis of fully protected peptide alcohols," Tetrahedron Letters. 40 (25):4663-4654.
Mutter et al. (1995) "Pseudo-prolines (psi Pro) for accessing 'inaccessible' peptides," Peptide Res. 8(3):145-153.
Rizzi et al. (2001) "Alcohols immobilization onto 2-chlorotritylchloride resin under microwave irradiation," Tetrahedron Letters. 52:2808-2811.
Wenschuh et al. (1995) "Stepwise automated solid phase synthesis of naturally occurring peptaibols using FMOC amino acid fluorides," The Journal of Organic Chemistry. 60(2):405-410.
Wu et al. (1999) "Direct solid phase synthesis of biologically active peptide alcohols," Journal of the Chinese Chemical Society. 46(2):135-138.
Yan et al. (2003) "Use of trichloroacetimidate linker in solid-phase peptide synthesis," The Journal of Organic Chemistry. 68(3):1161-1162.

(Continued)

*Primary Examiner* — Jeanette M Lieb
(74) *Attorney, Agent, or Firm* — Brian C. Trinque; Benjamin A. Vaughan; Lathrop Gage LLP

(57) ABSTRACT

The present application discloses peptides and peptaibols of high purity may be obtained by solid phase peptide synthesis using as the starting resin hydroxy amino acids, hydroxy amino acid amides, hydroxy amino alcohols or small peptides containing hydroxy amino acids attached to polymers through their side chain.

24 Claims, No Drawings

Specification includes a Sequence Listing.

(56) References Cited

OTHER PUBLICATIONS

Ziovas et al. (Aug. 21, 2012) "Abstract of Solid Phase Peptide Synthesis via Side-Chain Attachment on resins of Trityl and Benzhydryl Type," European Peptide Symposium, Sep. 7, 2012. J. Peptide Sci. Issue Supp. 51. Abstract No. P210.

International Preliminary Report on Patentability corresponding to International Patent Application No. PCT/IB2013/051544, dated Jul. 16, 2014.

* cited by examiner

SOLID PHASE PEPTIDE SYNTHESIS VIA SIDE CHAIN ATTACHMENT

RELATED APPLICATIONS

The present application is a divisional of U.S. patent application Ser. No. 13/772,793, filed Feb. 21, 2013, the entire contents of which is incorporated herein by reference.

SEQUENCE LISTING

This application contains a Sequence Listing in computer readable format. The Sequence Listing is provided as a file entitled 579620_DYT_006DV_ST25.txt created Jun. 14, 2018 which is 9,274 bytes in size. The information in the computer readable format of the Sequence Listing is incorporated herein by reference in its entirety.

SUMMARY

Peptides and peptaibols of high purity were obtained by solid phase peptide synthesis using as the starting resin hydroxy amino acids, hydroxy amino acid amides, hydroxy amino alcohols or small peptides containing hydroxy amino acids attached to polymers through their side chain.

Definitions and Abbreviations

"Hya" or "hydroxyl amino acid(s)" means amino acids that contain a hydroxyl (—OH) group.

N-terminus or amino terminus is the first amino acid in a peptide chain.

C-terminus or carboxy terminus is the last amino acid in the peptide chain as shown below.

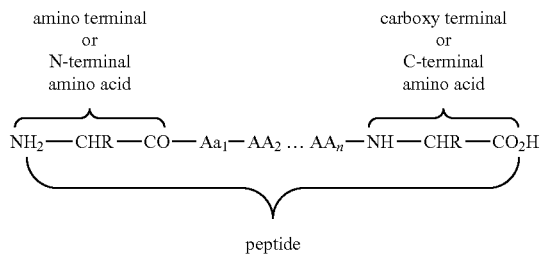

"P" or "solid support" or "resin" means an insoluble material containing a functional group(s) suitable to react and link with an amino acid or peptide. The solid support or resins are well known in the art.

"Alkyl" such as $C_{1-10}$alkyl or $C_{1-6}$alkyl, means a branched or unbranched fully saturated acyclic aliphatic hydrocarbon group (i.e. composed of carbon and hydrogen containing no double or triple bonds). In some embodiments, alkyls may be substituted or unsubstituted. Alkyls may include, but are not limited to methyl, ethyl, propyl, isopropyl, butyl, isobutyl, tert-butyl, pentyl, hexyl, and the like, and in some embodiment, each of which may be optionally substituted. Non-exclusive alkyl substituents may include $C_{1-3}$alkoxy, halo (F, Cl, Br or I), nitro, amino, —SH and —OH.

"Attachment" means the linking of an amino acid or a peptide or peptide derivative to an insoluble support.

"Hse" means homoserine; "Hnv" means hydroxylnorvaline.

"SPPS" or "solid phase peptide synthesis" means the synthesis of a peptide with the use of a resin as described herein.

"pNA" means 4-nitro anilide.

"DME" means dimethoxy ethane.

"Acid sensitive resin" means an insoluble material or resin containing a functional group(s) suitable to react and link with an amino acid or peptide, which may be cleaved from the peptide by acidic treatment.

"Acid sensitive protecting group" means a protecting group which may be cleaved from the amino acid or peptide or peptide derivative by acidic treatment or under acidic condition.

"Peptaibol" means a peptide which contain at its C-terminal position an amino alcohol instead of an amino acid or an amino acid amide.

"Step-by-step" means the method of peptide synthesis where any of the amino acids contained in the peptide chain is introduced individually and sequentially. The method may or may not involve an intermediate purification step.

"Protected peptide" means the peptide with all functional groups blocked or protected by protecting groups.

"Partially protected peptide" means the peptide which contains at least one functional group blocked or protected by a protecting group.

Solid phase peptide synthesis is traditionally performed by the attachment of the C-terminal amino acid through its α-carboxyl function on a suitable solid support and elongating the peptide chain towards the amino terminal of the peptide by adding sequentially the amino acid residues in the gradually growing peptide chain. Several hundred thousands of publications and patents describe this methodology and its application for the production of peptide pharmaceuticals.

In contrary to the attachment of the C-terminal carboxyl function, attachment of amino acids and peptides through an amino acid side chain on suitable resins and their application in SPPS is described very briefly, in particular in less than 30 publication and patents. Most of these publications describe the attachment of the amino acids through a side chain carboxyl function of Asp and Glu. To our knowledge, the reports of the side chain attachment of amino acids through a side chain hydroxyl function and application in peptide synthesis are limited: The side chain attachment of Fmoc-Hya-pNA (Formula A1) [A. Bernhardt, M. Drewello and M. Schutkowski, *The solid-phase synthesis of side-chain-phosphorylated peptide-4-nitroanilides J. Peptide Res.* 50, 1997. 143-152] and their use for the synthesis of short nitroanilide substrates, the synthesis of Fmoc-Hya-Oallyl esters (Formula A2 [L. Rizzi, K. Cendic, N. Vaiana, S. Romeo, *Alcohols immobilization onto 2-chlorotritylchloride resin under microwave irradiation*, Tetrahedron Letters 52 (2011) 2808-2811]) on 2-chlorotrityl resin with the aid of microwaves for application in the preparation of cyclic peptides and the synthesis of Fmoc-Tyr-O-methyl ester (Formula A3 [C. Cabrele, M. Langer and A. G. Beck-Sickinger, *Amino Acid Side Chain Attachment Approach and Its Application to the Synthesis of Tyrosine-Containing Cyclic Peptides, J. Org. Chem.* 1999, 64, 4353-4361]), attached on resins of the benzyl-type by the Mitsunobu redox-alkylation of the Tyr-phenoxy function and their application for the synthesis of short cyclic peptides. To our knowledge, the side chain attachment of Hse and Hyp have never been disclosed. In addition, the application of side chain attached Hya on acid sensitive resins for the solid phase synthesis of protected peptides, protected peptide fragments and of protected peptide amides and peptaibols have not been reported.

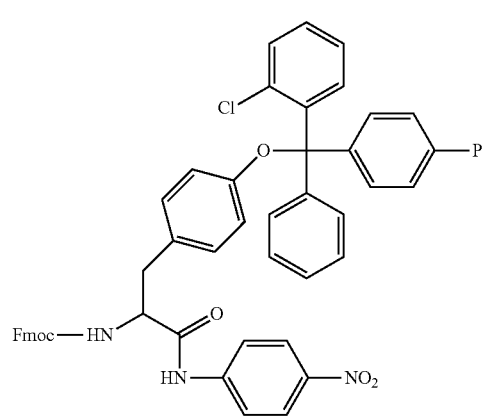

A1

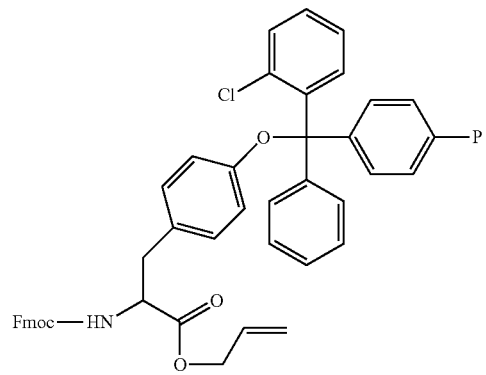

A2

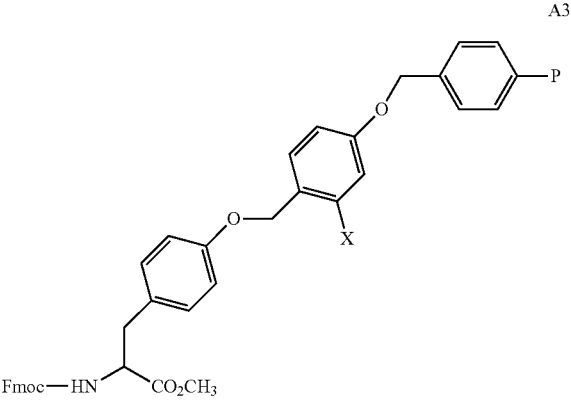

A3

Solid Phase Peptide Synthesis

In one embodiment, there is provided an improved synthesis of peptide acids, peptide amides, and peptaibols of pharmaceutical interest.

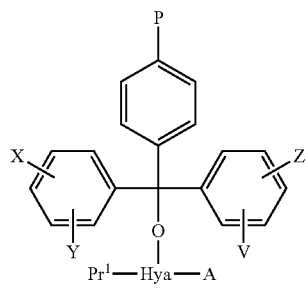

Formula I

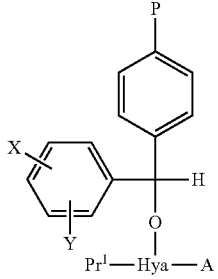

Formula II

In one aspect of the present application, the peptides were produced very efficiently in high yield and purity by attaching a hydroxy amino acid through its amino acid side chain, or a small peptide which contain in its sequence a hydroxy amino acid on a resin of the trityl or benzhydryl-type, resulting in amino acid-resin conjugates or peptide resin conjugates of Formula I-IV, wherein P is a solid-phase support selected from the supports used in solid phase peptide synthesis, $Pr^1$ is H or an amino protecting group selected from Fmoc, Boc, Trt, Dde and Alloc, wherein $Pr^2$ is an acid sensitive hydroxyl protecting group selected from Trt, Clt, Mmt, Mtt, Dpm and tBu, wherein Hya is a hydroxy amino acid selected from D- or L-Ser, Thr, Tyr, Hse, Hyp, Hnv etc., and A is OH, an acid sensitive alkoxy group selected from OTrt, OClt, OMmt, OMtt, ODpm and OtBu, $NH_2$, $NHR^1$, $NR^1R^2$ wherein $R^1$ and $R^2$ are independently an alkyl group a protected or semi protected peptide containing 1-10 amino acids in its sequence.

In another embodiment, we disclose that peptaibols, such as octreotide, were obtained by solid phase synthesis using the resin-bound amino alcohols of the Formula III-VI selected from amino alcohols which are derived from the naturally occurring hydroxy amino acids, wherein P, X, V, Z and $Pr^1$ are as defined above, wherein $R^3$, $R^4$ are alkyl, aryl or aralkyl groups, and $Pr^2$ is an acid sensitive protecting group of the trityl, benzhydryl or benzyl type.

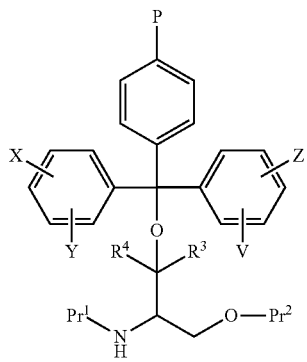

Formula III

Formula IV

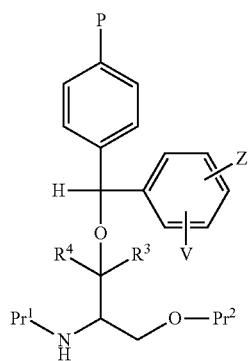

Formula V

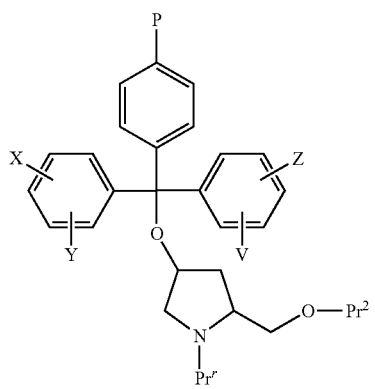

Formula VI

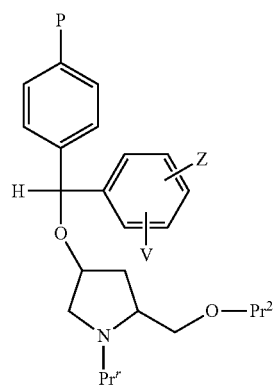

In addition we disclose for the first time that peptides prepared with the application of resins of the Formula I-IV, where the peptides are attached through the side chain hydroxyl function of a hydroxyamino acid on resins of the trityl type, may be cleaved from the resin by mild acidic treatment and wherein the side chain protecting groups of the tBu and benzyl-type remain intact. In one aspect, the cleavage from the resin occurs by the treatment with 1-3% acid solutions, such as TFA, diluted HCl solutions, optionally adding scavengers, in a solvent. In another aspect, the cleavage may be performed in a solvent such as DCM or acetone. Such partially protected peptides have been found to be useful in the synthesis of longer peptides by fragment condensation in solution or on solid phase. The present method expands the versatility of the application of the resins described herein, and also results in significantly improving the purity of the resulting pharmaceutical peptides, and at the same time, substantially reducing the cost of their synthesis.

Several peptides of pharmaceutical interest were produced as representative of the new process described herein, either by the step-by-step procedure or by fragment condensation in solution and on solid phase; or a combination thereof. The examples below are representative and do not limit their application in any way to other peptides.

Lanreotide:

In one embodiment, Lanreotide was produced by solid phase synthesis using resin-bound Thr-amide as shown below:

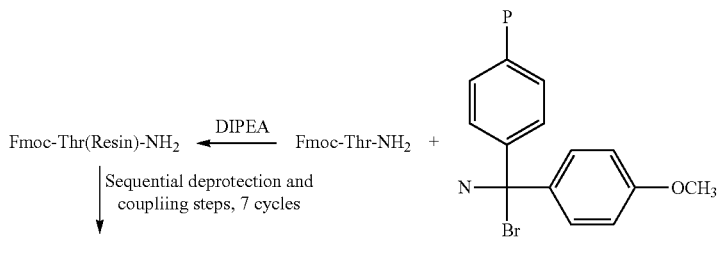

Fmoc-Thr(Resin)-NH₂ ⟵ DIPEA ⟵ Fmoc-Thr-NH₂ +

| Sequential deprotection and coupliing steps, 7 cycles

Boc-D-2-Nal-Cys(Trt)-Tyr(Clt)-D-Trp-Lys(Mtt)-Val-Cys(Trt)-Thr(Resin)-NH₂

| deprotection, cleavage from the resin and simultaneous iodine oxidation

H-D-2-Nal-Cys-Tyr-D-Trp-Lys-Val-Cys-Thr-NH₂

Lanreotide

Human Insulin B-Chain:

Optionally the human insulin B chain was synthesized by SPPS. In one aspect, the synthesis begins from the resin-bound Thr-t-butyl ester as described in the example, using the 4-methoxy benzhydryl resin. Optionally the synthesis may also be performed on solid phase by condensing the 1-8 partially protected Boc-Phe-Val-Asn(Trt)-Gln(Trt)-His(Trt)-Leu-Cys(Trt)-Gly-OH fragment with the resin-bound 9-30 fragment; or after the selective cleavage of the partially protected 9-30 fragment from the resin with condensation in solution of the 1-8 and 9-30 fragments.

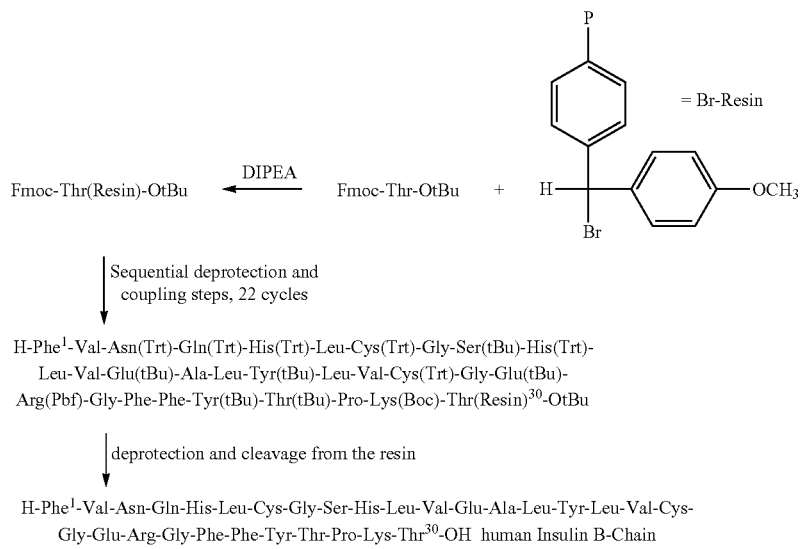

30

Salmon Calcitonin:

Optionally salmon calcitonin may be produced starting the synthesis from resin bound Fmoc-Thr-Pro-NH$_2$. The peptide chain is then elongated using Fmoc-amino acids.

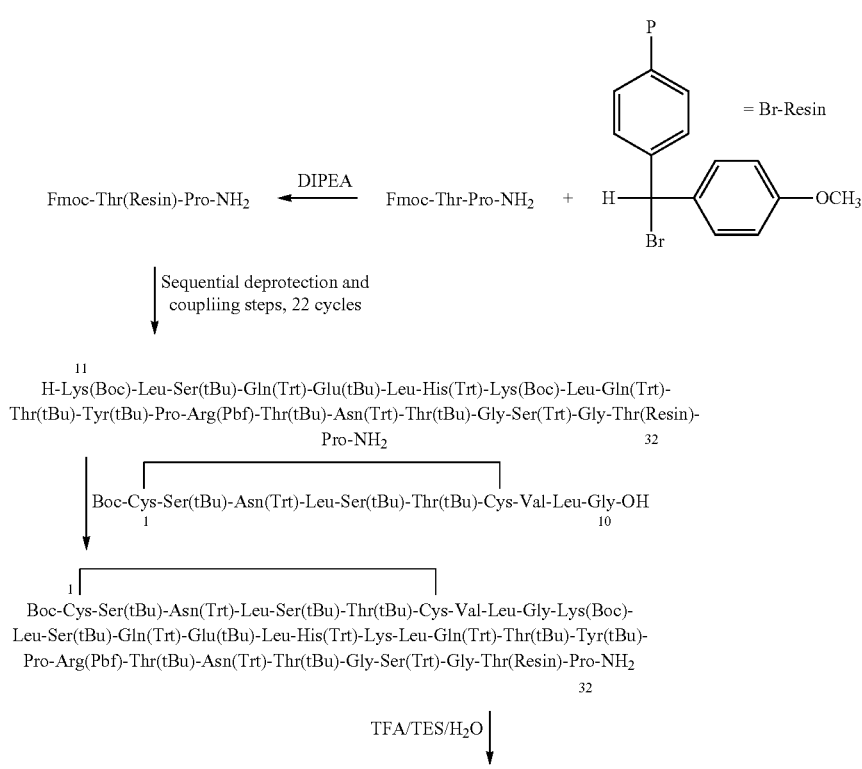

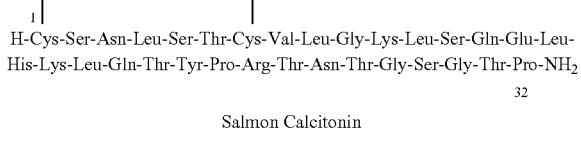

Salmon Calcitonin

Optionally the resin-bound salmon calcitonin is produced by fragment condensation on the resin as shown above, for example, or in solution as shown below using 2-4 fragments.

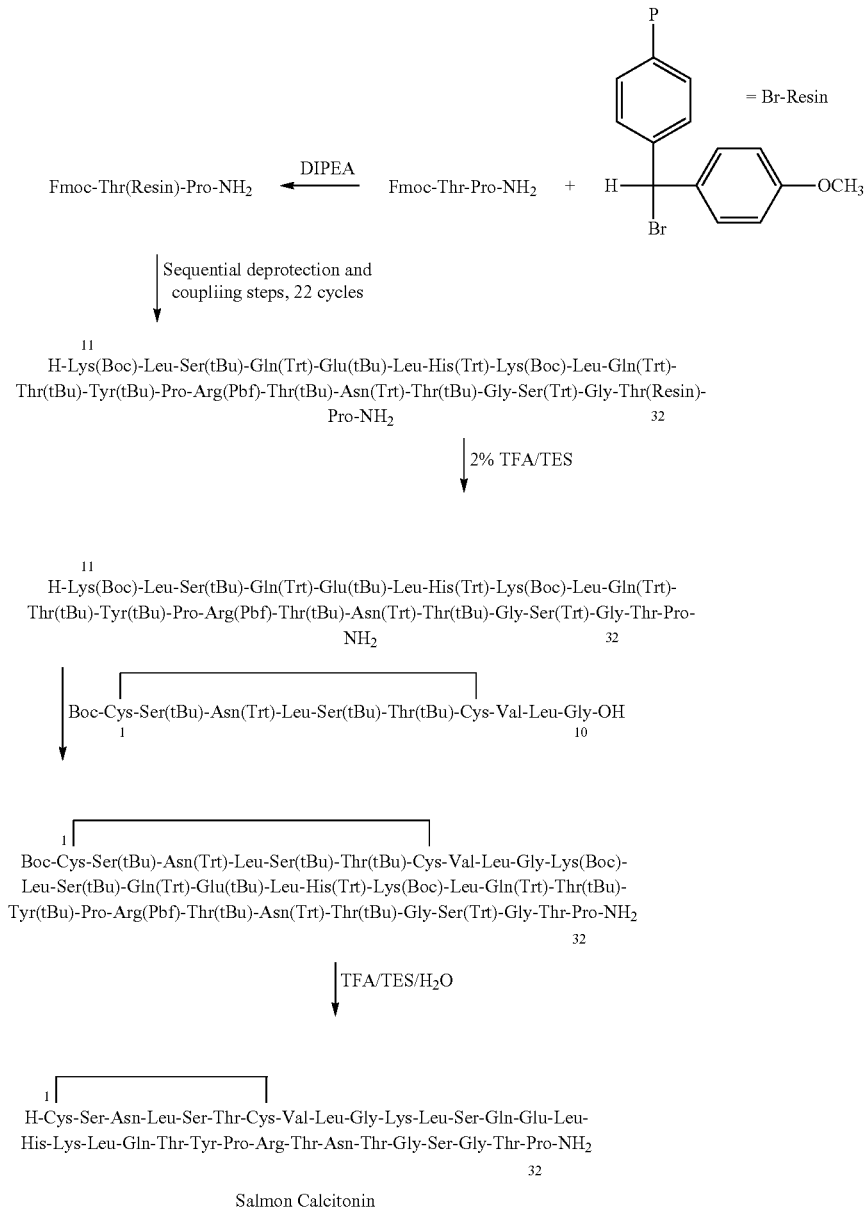

Salmon Calcitonin

Octreotide:

In another embodiment, octreotide was efficiently synthesized by the attachment of Fmoc-threoninol-OTrt to the 4-methoxybenzhydryl resin through the side chain of threoninol as shown below, followed by the octreotide chain assembly using Fmoc-amino acids and finally cleaving octreotide from the resin with subsequent or simultaneous Cys-oxidation. Fmoc-threoninol-OTrt is much easier to be produced than the Fmoc-Thr(tBu)-ol which may be attached onto the resin through the hydroxymethyl group of threoninol on a suitable resin. This is because H-Thr(OtBu)-ol, used as the starting material for the production of Fmoc-Thr(tBu)-ol, is much more difficult to be produced than Fmoc-threoninol-OTrt used in the attachment of threoninol through its side chain onto the resin.

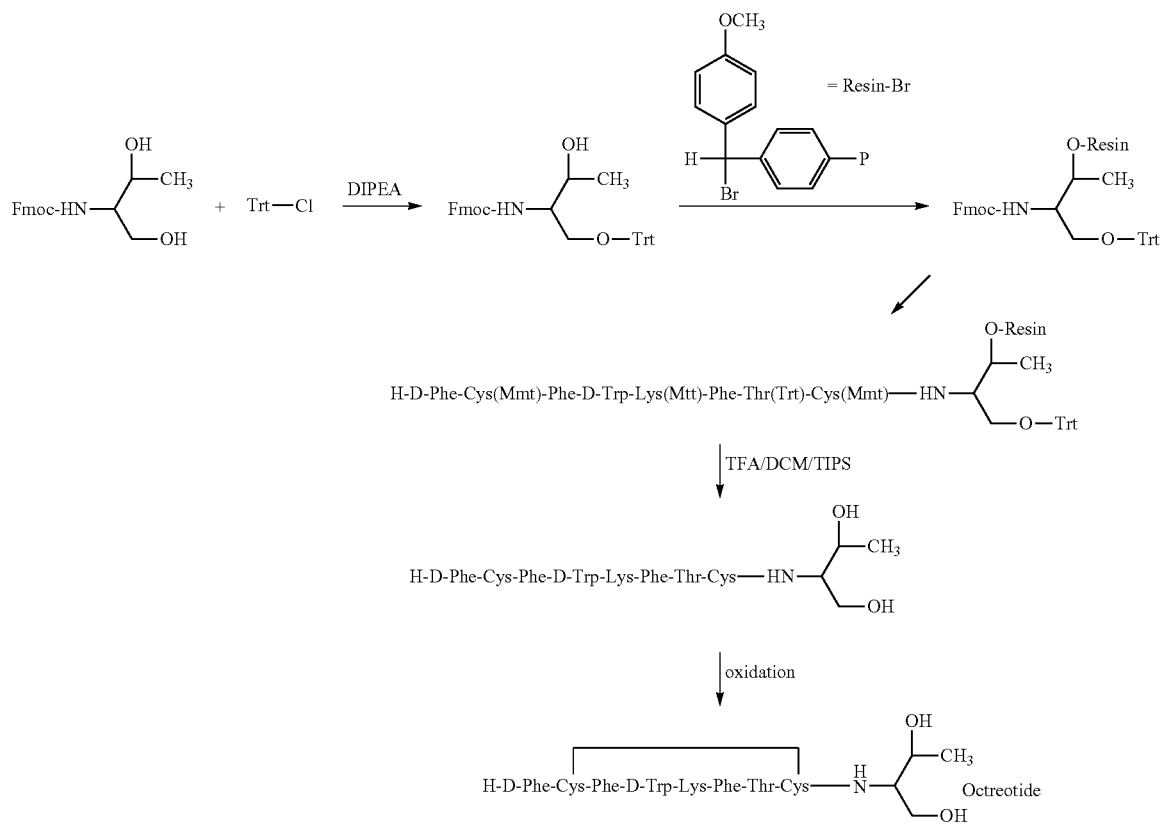

Exenatide:

In another example, Fmoc-Ser-NH$_2$ was attached through its side chain on trityl resin and used for the synthesis of exenatide. The synthesis may be performed by the step-by-step manner or by fragment condensation in solution after cleavage a partially protected exenatide fragment from the resin by mild acidic treatment or on solid phase, as described below. According to this method, most impurities typically formed during the synthesis of many Pro and Gly residues containing peptides are completely avoided and peptides of high purity are obtained. The method also allows the complete avoidance of impurities originating from the cleavage of peptides from peptide amide linkers using other methods known in the art, which significantly reduce the yields and purity of the peptide.

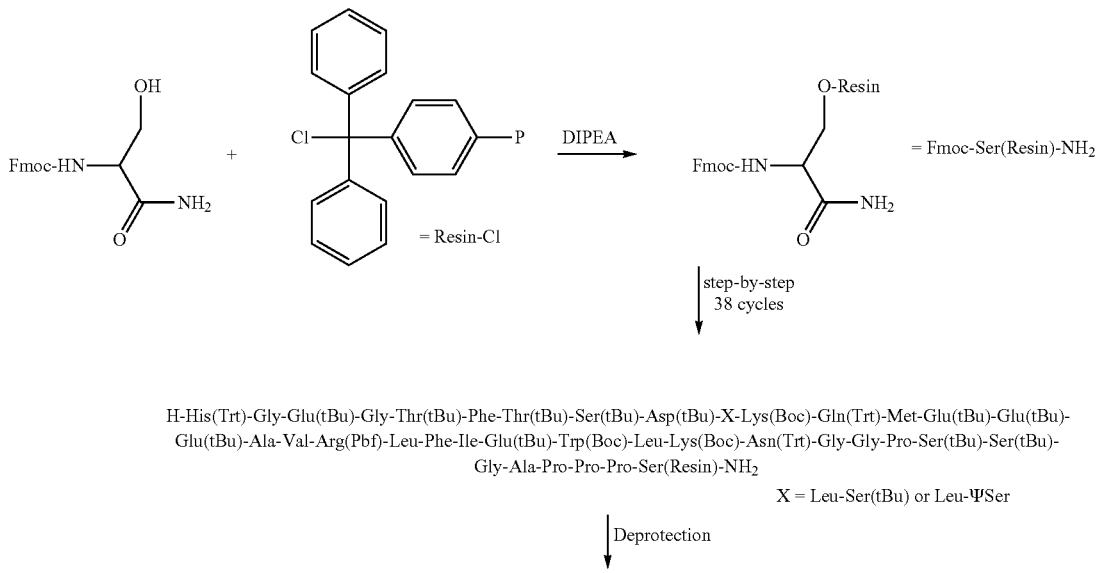

-continued

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-
Lys-Asn-Gly-Gly-Pro-Ser-Ser-Gly-Ala-Pro-Pro-Pro-Ser-NH$_2$

Exenatide

In one aspect, exenatide may be produced by cleavage of the partially protected peptide 12-39 from the resin and condensing it in solution as shown below with the partially protected 1-11 fragment. Alternatively, the condensation to obtain protected exenatide may be performed with the fragments 1-13 and 14-39.

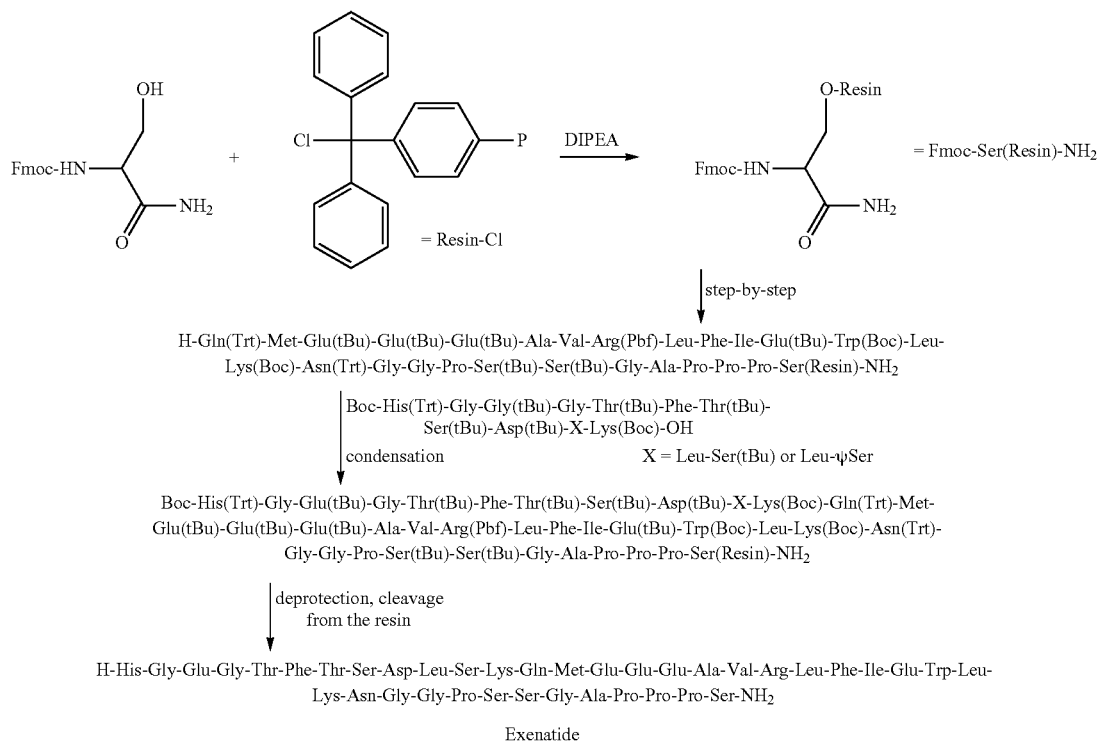

H-Gln(Trt)-Met-Glu(tBu)-Glu(tBu)-Glu(tBu)-Ala-Val-Arg(Pbf)-Leu-Phe-Ile-Glu(tBu)-Trp(Boc)-Leu-
Lys(Boc)-Asn(Trt)-Gly-Gly-Pro-Ser(tBu)-Ser(tBu)-Gly-Ala-Pro-Pro-Pro-Ser(Resin)-NH$_2$

| condensation | Boc-His(Trt)-Gly-Gly(tBu)-Gly-Thr(tBu)-Phe-Thr(tBu)-Ser(tBu)-Asp(tBu)-X-Lys(Boc)-OH X = Leu-Ser(tBu) or Leu-ψSer Boc-His(Trt)-Gly-Glu(tBu)-Gly-Thr(tBu)-Phe-Thr(tBu)-Ser(tBu)-Asp(tBu)-X-Lys(Boc)-Gln(Trt)-Met-
Glu(tBu)-Glu(tBu)-Glu(tBu)-Ala-Val-Arg(Pbf)-Leu-Phe-Ile-Glu(tBu)-Trp(Boc)-Leu-Lys(Boc)-Asn(Trt)-
Gly-Gly-Pro-Ser(tBu)-Ser(tBu)-Gly-Ala-Pro-Pro-Pro-Ser(Resin)-NH$_2$ deprotection, cleavage from the resin H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-
Lys-Asn-Gly-Gly-Pro-Ser-Ser-Gly-Ala-Pro-Pro-Pro-Ser-NH$_2$ Exenatide Pramlintide:

The method is also highly effective in the production of amylin peptides. In one aspect, the side chain attachment may be performed using one of the C-terminal Ser, Thr or Tyr residues of amylin or its derivatives such as pramlintide. The synthesis may be performed in the step-by-step manner or by fragment condensation in solution or on solid phase. By incorporating pseudoprolines (Ψ, see Mutter et al, *Peptide Res.* (1995 8, 145) into the growing peptide chain, the synthesis is accelerated and the purity of the peptide obtained is improved.

Fmoc-Tyr(Resin)-NH$_2$ step-by-step

Boc-Lys(Boc)-Cys(Trt)-Asn(Trt)-Thr(tBu)-Y-Cys(Trt)-Y-Gln(Trt)-Arg(Pbf)-Leu-Ala-Asn(Trt)-Phe-
Leu-Val-His(Trt)-X-Asn(Trt)-Asn(Trt)-Phe-Gly-Pro-Ile-Leu-Pro-Pro-Thr(tBu)-Asn(Trt)-Val-Gly-
Ser(tBu)-Asn(Trt)-Thr(tBu)-Tyr(Resin)-NH$_2$ Resin = 2-chlorotrityl resin

1%-TFA/DCM/I$_2$

-continued

Boc-Lys(Boc)-Cys-Asn(Trt)-Thr(tBu)-Y-Cys-Y-Gln(Trt)-Arg(Pbf)-Leu-Ala-Asn(Trt)-Phe-Leu-Val-His(Trt)-X-Asn(Trt)-Asn(Trt)-Phe-Gly-Pro-Ile-Leu-Pro-Pro-Thr(tBu)-Asn(Trt)-Val-Gly-Ser(tBu)-Asn(Trt)-Thr(tBu)-Tyr-NH$_2$

↓ deprotection

H-Lys-Cys-Asn-Thr-Ala-Thr-Cys-Ala-Thr-Gln-Arg-Leu-Ala-Asn-Phe-Phe-Leu-Val-His-Ser-Ser-Asn-Asn-Phe-Gly-Pro-Ile-Leu-Pro-Pro-Thr-Asn-Val-Gly-Ser-Asn-Thr-Tyr-NH$_2$ pramlintide X = Ser(tBu)-Ser(tBu) or Ser(tBu)-ΨSer
Y = Ala-Thr(tBu) or Ala-ΨThr
Ψ = pseudoprolin Alternatively, the synthesis of pramlintide may be performed in liquid phase with equal success concerning the purity and the yield of the obtained pramlintide. In one embodiment, the protected peptide which is bound on the resin through the side chain of Fmoc-Tyr-NH$_2$ may be quantitatively cleaved from the resin with the side chain protecting groups of the tBu-type remaining intact, using mild acidic treatment at various positions of the peptide chain. In one example, as shown below the partially protected 1-10 fragment prepared on the 2-chlorotrityl resin in the step by step manner was condensed successfully with the partially protected 11-37 fragment amide.

Pramlintide:

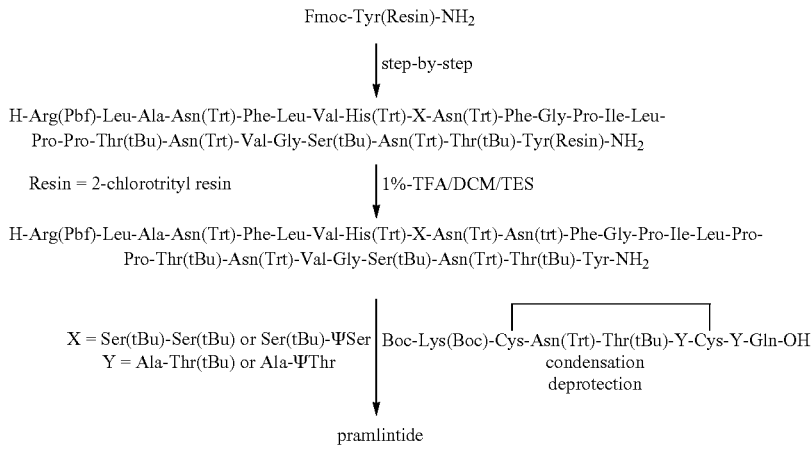

Tetracosactide (ACTH 1-24):

In another example, ACTH 1-24 was effectively prepared starting from resin-bound Fmoc-Tyr-Pro-OtBu by the step by step procedure or by condensing the 1-10 partially protected fragment in solution with the 11-24 fragment or with the resin-bound 11-24 fragment, as shown below.

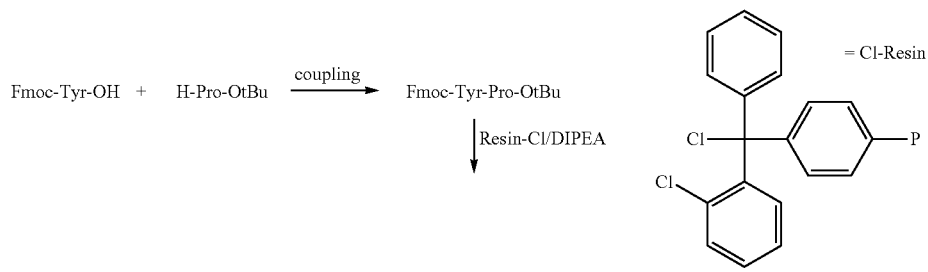

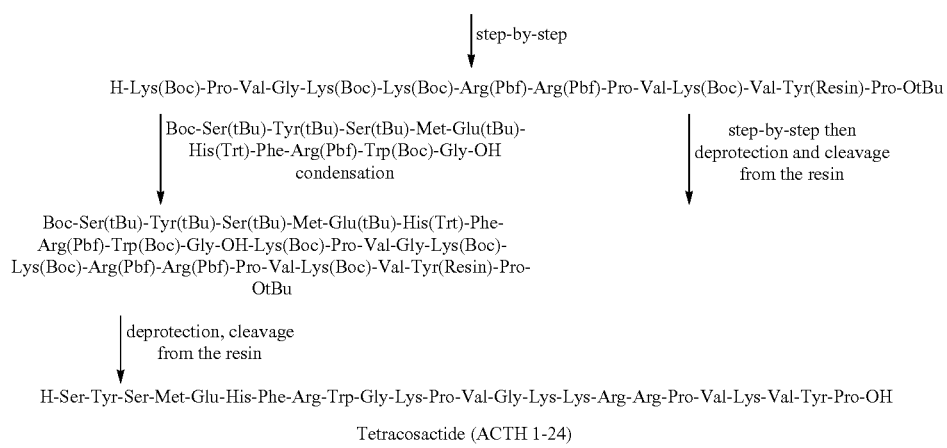

Bivalirudin:

In another example, bivalirudin was produced in high yield and high purity starting from resin-bound Fmoc-Tyr-Leu-OtBu, extending the peptide chain in the step-by-step manner with Fmoc-amino acids and finally deprotecting and cleaving the peptide from the resin as shown below.

Alternatively, bivalirudin was obtained by the condensation of protected fragments on the resin or by cleaving a partially protected peptide which contain 4-15 amino acid residues from the resin and condensing it in solution with a bivalirudin fragment which contain 5-16 amino acids. The bivalirudin synthesis by fragment condensation on the resin of the 1-10 partially protected bivalirudin fragment with the resin-bound 11-20 partially protected bivalirudin fragment is described below.

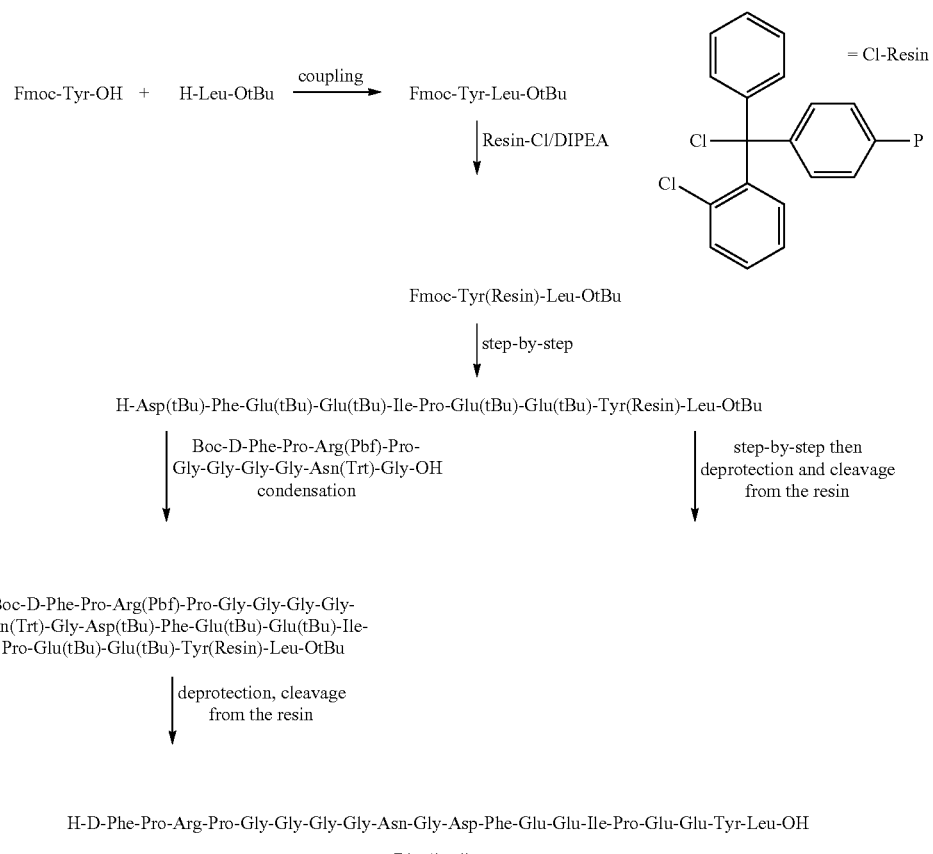

EXAMPLES

Example 1

Preparation of Fmoc-Thr(4-methoxybenzhydryl polystyryl)-OtBu

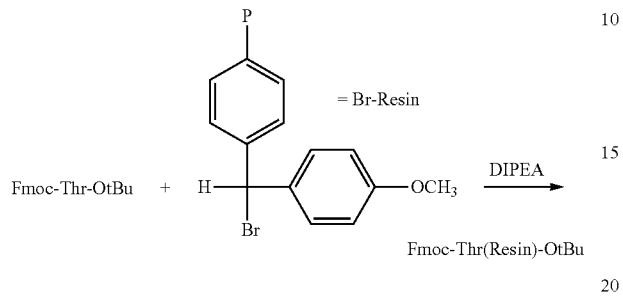

30 mmol Fmoc-Thr-OtBu prepared from H-Thr-OtBu by its reaction with Fmoc-OSu following conventional methods were reacted with 20 g (30 mmol) of 4-methoxybenzhydryl polystyrene resin (product of CBL-Patras) and 60 mmol DIPEA in 250 ml THF for 10 h at RT. To the mixture were then added 60 mmol methanol and the mixture was shaken for additional 4 h. The resin was filtered and washed 3× with THF/MeOH/DIPEA (85:10:5), 6× DMF, 4× IPA, 3× DEE and dried in vacuum to constant weight. 29 g of resin-bound Fmoc-Thr-OtBu were obtained with a loading of 0.95 mmol/g resin.

Example 2

Fmoc-Thr(4-methoxybenzhydryl polystyryl)-O-Clt

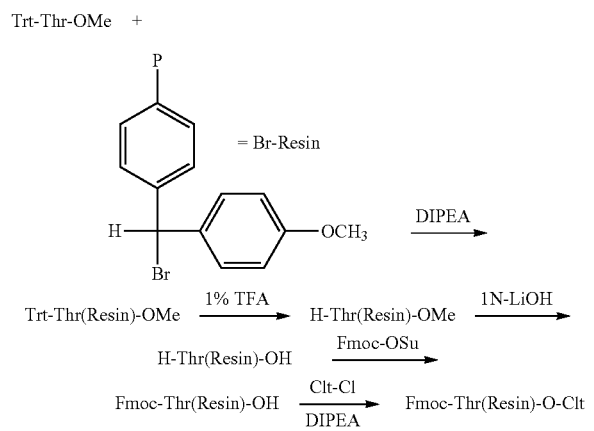

30 mmol Trt-Thr-OMe prepared from H-Thr-OMe by its reaction with Trt-Cl/Me$_3$SiCl and DIPEA following conventional methods were reacted with 20 g (30 mmol) of 4-methoxy 4'-polystyryl benzhydryl bromide resin (product of CBL-Patras) and 60 mmol DIPEA in 250 ml THF for 10 h at RT. To the mixture were then added 60 mmol methanol and the mixture was shaken for additional 4 h. The resin was filtered and washed 3× with THF/MeOH/DIPEA (85:10:5), 3× DCM, 3×1% TFA in DCM, 4× THF, 3×1N—LiOH in THF/Water/Methanol (70:15:15), 3× THF/Water (75:25) 4× DMF and then reacted for 2 h at RT with 60 mmol Fmoc-OSu and 30 mmol DIPEA, washed 3× DMF, 3× DCM and then reacted for 3 h at RT with 50 mmol Trt-Cl and 50 mmol DIPEA, washed 4× DMF, 6× DEE and dried in vacuum to constant weight. 32.3 g of resin-bound Fmoc-Thr-OtBu were obtained with a loading of 0.78 mmol/g resin.

Example 3

Fmoc-Throl(4-methoxy benzhydryl polystyryl)-O-Clt

A) Starting from Fmoc-Threoninol

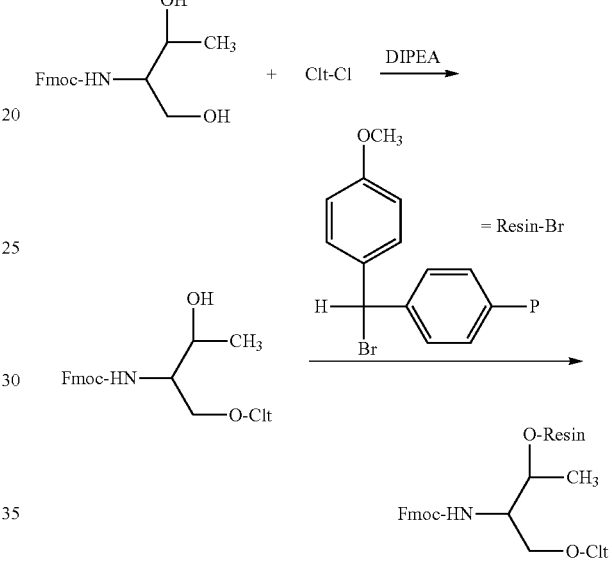

50 mmol commercial Fmoc-threoninol (CBL-Patras) in 350 ml DCM were reacted with 55 mmol monomeric Clt-Cl and 55 mmol DIPEA for 4 h at RT. The obtained mixture was extracted as usual with water and the DCM phase was dried over anhydrous sodium sulphate and filtered. To the resulting solution 30 g of 4-methoxy, 4-polystyryl benzhydryl bromide (CBL-Patras) were added and 50 mmol DIPEA and the resulting mixture was stirred for 4 h at RT. The resin was filtered and washed 6×DMF, 4×IPA and 4× DEE and dried in vacuum to constant weight. 38.4 g of resin-bound Fmoc-threoninol were obtained with a loading of 0.82 mmol/g.

B) Starting from Trt-Thr(Resin)-OMe

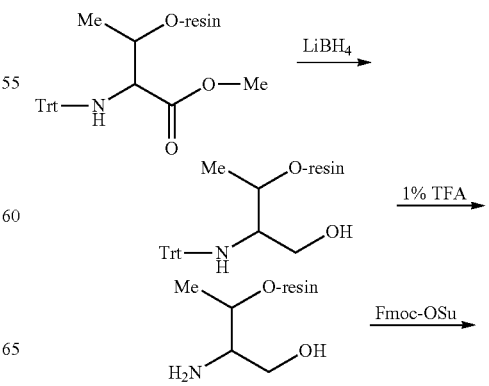

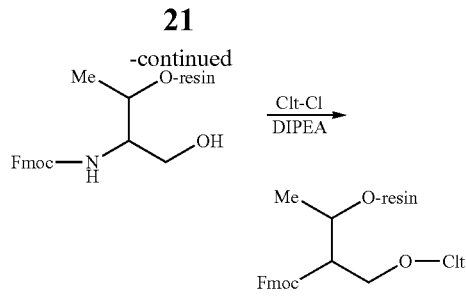

30 mmol Trt-Thr-OMe prepared from H-Thr-OMe by its reaction with Trt-Cl/Me₃SiCl and DIPEA following conventional methods were reacted with 20 g (30 mmol) of 4-methoxy 4'-polystyryl benzhydryl bromide resin (product of CBL-Patras) and 60 mmol DIPEA in 250 ml THF for 10 h at RT. To the mixture were then added 60 mmol methanol and the mixture was shaken for additional 4 h. The resin was filtered and washed 3× with THF/MeOH/DIPEA (85:10:5), 5× THF, and then reacted with 30 mmol LiBH₄ in THF. The resin was then filtered and washed 6× THF, 4× DCM, 6×1% TFA in DCM, 3× with DMF/DIPEA (97:3) and then reacted for 2 h at RT with 60 mmol Fmoc-OSu and 30 mmol DIPEA, washed 3× DMF, 3× DCM and then reacted for 3 h at RT with 50 mmol Clt-Cl and 50 mmol DIPEA, washed 4× DMF, 6× IPA and 6× DEE and dried in vacuum to constant weight. 34.7 g of resin-bound Fmoc-Throl-O-Clt were obtained with a loading of 0.74 mmol/g resin.

Example 4

Fmoc-Ser(trityl Resin)-NH₂

50 mmols of Fmoc-Ser-NH₂, prepared according to standard procedures known in the art, were dissolved in 0.5 liter of DCM. To the suspension 30 g of Trityl chloride resin (36 mmol) were added and 65 mmol DIPEA and the mixture was stirred for 6 h at RT. Then and then 25 ml methanol and 30 mmol DIPEA were added and the mixture was stirred for additional 2 h at RT. The resin was then filtered and washed 3× with DCM/MeOH/DIPEA (90:5:5), 5× DMF, 4× IPA, 4× DEE and dried in vacuum to constant weight. 41.1 g of Fmoc-Ser-NH₂-containing resin were obtained with a loading of 0.71 mmol/g.

Example 5

Fmoc-Tyr(2-chlorotrityl Resin)-NH₂

Following the above procedure, 50 mmol Fmoc-Tyr-NH₂ and 30 g 2-CTC chloride resin gave 43.7 g resin with a loading of 0.81 g Tyr/g resin.

Example 6

Fmoc-Hyp(4-methyl benzhydryl Resin)-NH₂

Following the above procedure 50 mmol Fmoc-Hyp-NH₂ and 30 g 4-methyl benzhydryl bromide resin gave 39.8 g resin with a loading of 0.49 g Hyp/g resin.

Example 7

Fmoc-Thr(4-methoxybenzhydryl Resin)-Pro-NH₂

50 mmols of Fmoc-Thr-Pro-NH₂ prepared from coupling of Fmoc-Thr(tBu)-OH with H-Pro-NH₂ according to standard procedures known in the art, were dissolved in 0.5 liter of DME. To the resulting solution 30 g of 4-methoxy benzhydryl bromide resin (45 mmol) were added and 65 mmol DIPEA and the mixture was stirred for 6 h at RT. Then 25 ml methanol and 50 mmol DIPEA were added and the mixture was stirred for additional 2 h at RT. The resin was then filtered and washed 3× with DME/MeOH/DIPEA (90:5:5), 5× DMF, 4× IPA, 4× DEE and dried in vacuum to constant weight. 44.5 g of Fmoc-Thr-Pro-NH₂ containing resin with a loading of 0.77 mmol/g was obtained.

Example 8

Fmoc-Tyr(2-chlorotrityl Resin)-Pro-OtBu 50 mmols of Fmoc-Tyr-Pro-OtBu were prepared according to standard procedures known in the art, were dissolved in 0.5 liter of DCM. To the resulting solution 30 g of 2-chlorotrityl chloride resin (48 mmol) were added and 65 mmol DIPEA and the mixture was stirred for 12 h at RT. Then 25 ml methanol and 50 mmol DIPEA were added and the mixture was stirred for additional 2 h at RT. The resin was then filtered and washed 3× with DCM/MeOH/DIPEA (90:5:5), 5× DMF, 4× IPA, 4× DEE and dried in vacuum to constant weight. 44.5 g of Fmoc-Tyr-Pro-OtBu containing resin with a loading of 0.64 mmol/g was obtained.

Example 9

Fmoc-Tyr(2-chlorotrityl Resin)-Leu-OtBu 50 mmols of Fmoc-Tyr-Leu-OtBu, prepared according to standard procedures known in the art, were dissolved in 0.5 liter of THF. To the resulting solution 30 g of 2-CTC chloride resin (48 mmol) were added and 65 mmol DIPEA and the mixture was stirred for 12 h at 60° C. Then 25 ml methanol and 50 mmol DIPEA were added and the mixture was stirred for additional 2 h at RT. The resin was then filtered and washed 3× with DCM/MeOH/DIPEA (90:5:5), 5× DMF, 4× IPA, 4× DEE and dried in vacuum to constant weight. 44.5 g of Fmoc-Tyr-Leu-OtBu-containing resin with a loading of 0.64 mmol/g was obtained.

Example 10

Solid-phase synthesis of peptides and protected peptide segments.
General Procedure.
A1. Preparation of Loaded 2-Chlorotrityl Resins, General Procedure
2-Chlorotrityl chloride resin (CTC-Cl) (100 g; loading 1.6 mmol/g) of CBL-Patras, is placed in a 2 L peptide synthesis reactor and is swollen with 700 mL dichloromethane (DCM):dimethylformamide (DMF) 1:1 for 30 min at 25° C. The resin is filtered and a solution of 100 mmol Fmoc-amino acid and 300 mmol diisopropylethylamine (DIEA) in 500 mL DCM is added. The mixture is stirred under nitrogen for 2 hours at 25° C. Then, the remaining active sites of the 2-CTC resin are neutralised by adding 10 mL of methanol (MeOH) and reacting for 1 hour. The resin is filtered and washed twice with 400 mL DMF. The resin is filtered and treated twice with 500 mL 25% by volume of piperidine in DMF for 30 min. The resin is then washed four times with 500 mL DMF. The resin is deswelled with 3 washes with 500 mL of isopropanol (IPA). The resin is dried to constant weight. On the resin was bound the 70-95% of the mmol of the used amino acid.

B. Solid-Phase Synthesis, a General Protocol

The solid-phase synthesis was performed at 24° C. with 1.0 g amino acid or peptide esterified to the resin of the trityl or benzhydryl type or attached through its side chain as described in Part A or in the examples Example 1. The following protocol was used in the synthesis.

B1. Swelling of the Resin

The resin was placed in a 15 ml reactor and treated twice with 7 mL NMP, followed by filtration.

B2. Activation of the Amino Acid

The amino acid (3.0 equiv.) and 1-hydroxybenzotriazole (4.0 equiv.) was weighted and dissolved in a reactor with 2.5 their volume in NMP and cooled to 0° C. DIC was then added (3.0 equiv.) and the mixture was stirred for 15 min.

B3. Coupling

The solution which was prepared in B2 was then added to the B1 reactor. The reactor was washed once with one volume of DCM and was added to the reactor which was stirred for 1-3 h at 25°–30° C. In a sample the Kaiser Test was performed to determine the completion of the reaction. If the coupling reaction was not completed after 3 h (positive Kaiser Test), the reaction mixture was filtered and recoupled with a fresh solution of activated amino acid. After completion of the coupling the reaction mixture was filtered and washed 4 times with NMP (5 volumes per wash).

B4. Removal of the Fmoc-Group

The resulting resin in B3 was filtered and then treated for 30 min with 5 mL of a solution which contained 25% by volume of piperidine. The resin is then washed three times with 5 mL NMP.

B5. Elongation of the Peptide Chain

After the incorporation of each amino acid the steps B1-B5 were repeated until the completion of the peptide chain.

For the introduction of each individual amino acid the following Fmoc-amino acids were used: Fmoc-Ala-OH, Fmoc-Arg(Pbf)-OH, Fmoc-Asn-OH, Fmoc-Asn(Trt)-OH, Fmoc-D-Cys(Trt)-OH, Fmoc-Cys(Trt)-OH, Fmoc-Gln-OH, Fmoc-Gln(Trt)-OH, Fmoc-Glu(tBu)-OH, Fmoc-Gly-OH, Fmoc-His(Trt)-OH, Fmoc-Hyp(tBu)-OH, Fmoc-Ile-OH, Fmoc-Leu-OH, Fmoc-Met-OH, Fmoc-D-Phe-OH, Fmoc-Phe-OH, Fmoc-Pro-OH, Fmoc-Ser(tBu)-OH, Fmoc-Ser(Trt)-OH, Fmoc-Thr(tBu)-OH, Fmoc-Ser(Trt)-OH, Fmoc-D-Trp-OH, Fmoc-Trp-OH, Fmoc-D-Trp(Boc)-OH, Fmoc-Trp(Boc)-OH, Fmoc-Tyr(tBu)-OH, Fmoc-Tyr(Clt)-OH, Fmoc-Val-OH, Boc-D-Cys(Trt)-OH, Boc-His(Trt)-OH, Boc-Lys(Boc)-OH, Boc-D-2-Nal-OH, Boc-D-Phe-OH, Boc-Ser(tBu)-OH.

C. General method for the acidic cleavage from the CTC-resin of peptides and of protected peptide segments, which contain Fmoc- or Boc-groups on their N-terminus.

The resin-bound peptide or peptide segment which was produced as described above in B1-B5 was washed 4 times with 5 mL NMP, 3 times with 5 ml IPA and finally 5 times with 7 ml DCM to remove completely any residual NMP or other basic components. The resin was then cooled to 0° C., filtered from DCM and was treated twice with a solution of 10 mL 1-2% TFA/DCM at 5° C. The mixture is then stirred 20 min at 0° C. and filtered. The resin is then washed three times with 10 mL DCM. Pyridine is then added to the filtrates (1.3 equiv. relative to TFA) to neutralize the TFA. The cleavage solution in DCM is then mixed with an equal volume of water. The resulting mixture is distilled at reduced pressure to remove DCM (350 torr at 28° C.). The peptide or peptide segment precipitated after the removal of DCM. The resulting peptide is washed then with water and dried at 30-35° C. under 15 Torr vacuum.

Example 11

Synthesis of resin-bound protected peptides by the condensation of an N-terminal protected fragment with a resin-bound C-terminal protected fragment.

General Procedure

To a solution of 0.15 mmol/ml of an N-terminal protected peptide fragment in DMSO/DCM (95:5) are added 0.2 mmol HOBt and the resulting solution is cooled to 5° C. Then 0.14 mmol DIC were added and the mixture is stirred for 20 min at 15° C. and added then to 0.1 mmol of a resin-bound C-terminal fragment and stirred for additional 6 h at RT. The completion of the condensation reaction is checked by the Kaiser test. In the cases where the Kaiser test remained blue a second condensation was performed in order to drive the condensation into completion.

Example 12

Synthesis of partially protected peptides by the condensation of an N-terminal protected fragment with a C-terminal protected fragment in solution.

General Procedure

To a solution of 0.15 mmol/ml of an N-terminal protected fragment in DCM are added 0.2 mmol HOBt and the resulting solution is cooled to 5° C. Then 0.15 mmol EDAC were added and the mixture is stirred for 20 min at 15° C. and added then to 0.15 mmol of a C-terminal protected fragment and stirred for additional 2-5 h at RT. The completion of the condensation reaction is checked by HPLC. In the cases where an incomplete condensation was observed an additional portion of 0.015 mmol EDAC was added and the reaction was left to proceed for an additional hour at RT.

Example 13

Deprotection and simultaneous cleavage from the resin of peptides.

General Method 1.00 g of the protected resin-bound peptide, produced as described above is treated with 20 mL TFA/DTT/water (90:5:5) for 3 h at 5° C. and for 1 h at 15° C. The resin is then washed 3× with the cleavage solution and the combined filtrates are then concentrated in vacuum and crude peptide is precipitated by the addition of ether, washed several times with ether and dried in vacuum until constant weight over KOH.

Example 14

Peptide Deprotection
General Method 1.00 g of the protected peptide, produced as described above was treated with 20 mL TFA/DTT/water (90:5:5) for 3 h at 5° C. and for 1 h at 15° C. The resulting solution is concentrated in vacuum and then the deprotected peptide was precipitated by the addition of diisopropylether and washed three times with 10 mL diisopropylether. The resulting solid was dried in vacuum (25° C., 15 Torr) until constant weight under KOH.

Example 15

Purification of Crude Peptides. Isolation of Peptides.
General Procedure

The solution of the peptides obtained as described above was concentrated in vacuum and ice water and ether were added. After separation of the organic layer the remaining water solution of the peptide was extracted for additional two times with ether and the resulting solution was sparged with nitrogen or helium, filtered and directly loaded on a semipreparative column 10×25 cm, Lichrospher 100, RP-18, 12 micron (Merck); Phase A=1%-TFA in acetonitrile, phase B=1%-TFA in water; or Kromasil. HPLC fractions containing the purified peptide were concentrated in vacuum to remove as much as possible the contained acetonitrile and lyophilized using a standard lyophilisation program.

Examples 16 to 23, as noted below, were performed using the above procedures to prepare the listed compounds.

Example 16

Lanreotide

Example 17

Insulin B-chain

Example 18

Salmon Calcitonin

Example 19

Octreotide

Example 20

Exenatide

Example 21

Pramlintide

Example 22

Tetracosactide (ACTH 1-24)

Example 23

Bivalirudin

What is claimed is:

1. A peptide resin conjugate of the formula E-D-2-Nal-Cys(A)-Tyr(C)-D-Trp(F)-Lys(E)-Val-Cys(A)-Thr(Resin)-NH$_2$ wherein:
   D-designates the chirality of the amino acid that follows as a D-amino acid;
   each A is independently a thiol protecting group selected from Trt, Mmt, Acm, and StBu;
   C is a hydroxy protecting group selected from 2-chlorotrityl (Clt), Trt, and tBu;
   F is H or Boc;
   E is an amino protecting group selected from Mtt, Mmt, Trt, and Boc; and
   Resin is H or an acid labile resin suitable for solid-phase peptide synthesis.

2. A process for preparing lanreotide comprising:
   treating the peptide resin conjugate of claim 1 with a mild acid selected from solutions of trifluoracetic acid optionally containing scavengers; and
   oxidizing the resulting peptide using an oxidizing agent selected from air, hydrogen peroxide, DMSO, and iodine.

3. A process for preparing lanreotide comprising treating the peptide resin conjugate of claim 1 with a mild acid such as a solution of trifluoracetic acid containing iodine.

4. A peptide of the formula E-Phe-Val-Asn(A)-Gln(A)-His(A)-Leu-Cys(B)-Gly-Ser(C)-His(A)-Leu-Val-Glu(C)-Ala-Leu-Tyr(C)-Leu-Val-Cys(A)-Gly-Glu(C)-Arg(D)-Gly-Phe-Phe-Tyr(C)-Thr(C)-Pro-Lys(E)-Thr(Resin)-O-C wherein:
   A is H or a carboxamido or imidazol protecting group selected from Trt, Mtt, and Mmt;
   B is a Cys protecting group selected from Mmt, Trt, Acm, and StBu;
   C is a hydroxy, carboxyl or phenoxy protecting group selected from tBu, Trt, and 2-chlorotrityl (Clt);
   D is a guanidine protecting group selected from Pbf and Pmc;
   E is H or an amino protecting group selected from Fmoc, Boc, Trt, Nps, Mtt, Mmt, and 2-chlorotrityl (Clt); and
   Resin is H or an acid labile resin suitable for solid-phase peptide synthesis.

5. A process for preparing an insulin B-chain, wherein the process comprises contacting the peptide resin conjugate of claim 4 with an acid solution, such as trifluoroacetic acid solutions in dichloromethane, optionally containing scavengers.

6. A peptide resin conjugate of the formula E-Ser(C)-His(A)-Leu-Val-Glu(C)-Ala-Leu-Tyr(C)-Leu-Val-Cys(B)-Gly-Glu(C)-Arg(D)-Gly-Phe-Phe-Tyr(C)-Thr(C)-Pro-Lys(E)-Thr(Resin)-O- wherein:
   A is a carboxamido or imidazol protecting group selected from Trt, Mtt, and Mmt;
   B is a Cys protecting group selected from Mmt, Trt, Acm, and StBu;
   each C is independently a hydroxy, carboxyl or phenoxy protecting group selected from tBu, Trt, and 2-chlorotrityl (Clt);
   D is H or a guanidine protecting group selected from Pbf and Pmc;
   E is H or an amino protecting group selected from Fmoc, Boc, Trt, Nps, Mtt, Mmt, and 2-chlorotrityl (Clt); and
   Resin is H or an acid labile resin suitable for solid-phase peptide synthesis.

7. A process for the preparation of insulin B-chain, the process comprising:
   condensation of the peptide resin conjugate of claim 6 with a 1-8 protected insulin fragment Boc-Phe-Val-Asn(A)-Gln(A)-His(A)-Leu-Cys(B)-Gly-OH, wherein;
   each A is independently a carboxamido or imidazol protecting group selected from Trt, Mtt, and Mmt; and
   B is a Cys protecting group selected from Mmt, Trt, Acm, and StBu.

8. A peptide resin conjugate of the formula E-Cys(B)-Ser(C)-Asn(A)-Leu-Ser(C)-Thr(C)-Cys(B)-Val-Leu-Gly-Lys(E)-Leu-Ser(C)-Gln(A)-Glu(C)-Leu-His(A)-Lys(E)-Leu-Gln(A)-Thr(C)-Tyr(C)-Pro-Arg(D)-Thr(C)-Asn(A)-Thr(C)-Gly-Ser(C)- Gly-Thr(Resin)-Pro-NH$_2$, wherein:
   each A is independently a carboxamido or imidazol protecting group selected from Trt, Mtt, and Mmt;
   each B is independently a Cys protecting group selected from Mmt, Trt, Acm, and StBu;
   each C is independently a hydroxyl, carboxy, or phenoxy protecting group selected from of tBu, Trt, and 2-chlorotrityl (Clt);
   D is a guanidine protecting group selected from Pbf and Pmc;
   each E is independently H or an amino protecting group selected from Fmoc, Boc, Trt, Nps, Mtt, Mmt, and 2-chlorotrityl (Clt); and
   Resin is H or an acid labile resin suitable for solid-phase peptide synthesis.

9. A process for producing salmon calcitonin, the process comprising:

treating the peptide resin conjugate of claim 8 with a mild acid such as a solution of trifluoracetic acid optionally containing scavengers;
oxidizing the obtained peptide solution using a suitable oxidizing agent selected from air, hydrogen peroxide, DMSO, and iodine;
deprotecting the peptide;
purifying the peptide by chromatography; and
lyophilizing the peptide.

10. A process for producing salmon calcitonin, the process comprising:
treating the peptide resin conjugate of claim 8 with a mild acid such as a solution of trifluoracetic acid;
oxidizing the peptide with iodine;
deprotecting the peptide by treatment with acids such as a solution of trifluoroacetic or hydrochloric acid optionally containing scavengers; and
purifying by chromatography and lyophilizing the salmon calcitonin peptide.

11. A process for the preparation of salmon calcitonin the process comprising: condensing the partially protected 11-32 peptide resin conjugate fragment of salmon calcitonin of the formula H-Lys(E)-Leu-Ser(C)-Gln(A)-Glu(C)-Leu-His(A)-Lys(E)-Leu-Gln(A)-Thr(C)-Tyr(C)-Pro-Arg(D)-Thr(C)-Asn(A)-Thr(C)-Gly-Ser(C)-Gly-Thr(Resin)-Pro-NH$_2$ with a 1-10 partially protected fragment of salmon calcitonin of the formula E-Cys(B)-Ser(C)-Asn(A)-Leu-Ser(C)-Thr(C)-Cys(B)-Val-Leu-Gly-OH; wherein
each A is independently a carboxamido or imidazol protecting group selected from Trt, Mtt, and Mmt;
each B is independently a Cys protecting group selected from Mmt, Trt, Acm, and StBu;
each C is independently a hydroxyl, carboxy or phenoxy protecting group selected from tBu, Trt, and 2-chlorotrityl (Clt);
D is H or a guanidine protecting group selected from Pbf and Pmc;
each E is independently H or an amino protecting group selected from Fmoc, Boc, Trt, Nps, Mtt, Mmt, and 2-chlorotrityl (Clt); and
Resin is H or an acid labile resin suitable for solid-phase peptide synthesis.

12. A partially protected peptide resin conjugate of the formula E-His(A)-Gly-Glu(C)-Gly-Thr(C)-Phe-Thr(C)-Ser(C)-Asp(C)-X-Lys(E)-Gln(A)-Met-Glu(C)-Glu(C)-Glu(C)-Ala-Val-Arg(D)-Leu-Phe-Ile-Glu(C)-Trp(F)-Leu-Lys(E)-Asn(A)-Gly- Gly-Pro-Ser(C)-Ser(C)-Gly-Ala-Pro-Pro-Pro-Ser(Resin)-NH$_2$ wherein:
X is Leu-Ser(tBu) or Leu-ψSer;
each A is independently H or a carboxamido or imidazol protecting group selected from Trt, Mtt, and Mmt;
each C is independently a hydroxy, carboxyl, or phenoxy protecting group selected from tBu, Trt, and 2-chlorotrityl (Clt);
D is H or a guanidine protecting group elected from Pbf and Pmc;
each E is independently H or an amino protecting group selected from Fmoc, Boc, Trt, Nps, Mtt, Mmt, and 2-chlorotrityl (Clt);
F is H or Boc; and
Resin is an acid labile resin suitable for solid-phase peptide synthesis.

13. A partially protected peptide resin conjugate Y-Glu(C)-Glu(C)-Ala-Val-Arg(D)-Leu-Phe-Ile-Glu(C)-Trp(F)-Leu-Lys(E)-Asn(A)-Gly-Gly-Pro-Ser(C)-Ser(C)-Gly-Ala-Pro-Pro-Pro-Ser(Resin)-NH$_2$ that is the exenatide fragments 12-39, 13-39, 14-39, wherein:

Y is H, E-Glu(C), E-Met-Glu(C), E-Gln(A)-Met-Glu(C) or E-Lys(E')-Gln(A)-Met-Glu(C); wherein:
each A is independently H or a carboxamido protecting group selected from Trt, Mtt, and Mmt;
E and E' are each independently H or an amino protecting group selected from Fmoc, Boc, Trt, Nps, Mtt, Mmt, and 2-chlorotrityl (Clt);
F is H or Boc;
each C is independently a hydroxy or carboxyl protecting group selected from tBu, Trt, and 2-chlorotrityl (Clt);
D is H or a guanidine protecting group selected from Pbf and Pmc; and
Resin is H or an acid labile resin suitable for solid-phase peptide synthesis.

14. A partially protected peptide that is E-His(A)-Gly-Glu(C)-Gly-Thr(C)-Phe-Thr(C)-Ser(C)-Asp(C)-X-Y in particular sequences corresponding to the exenatide fragments 1-11, 1-13, 1-14 and 1-15, wherein:
X is Leu-Ser(tBu) or Leu-ψSer;
E is an amino protecting group selected from Fmoc, Boc, Trt, Nps, Mtt, Mmt, and 2-chlorotrityl (Clt);
A is H, a carboxamido or imidazol protecting group selected from Trt, Mtt, and Mmt;
each C is independently a hydroxy or carboxyl protecting group selected from tBu, Trt, and 2-chlorotrityl (Clt); and
Y is OZ, Lys(E)-Gln(A)-OZ, Lys(E)-Gln(A)-Met-OZ, Lys(E)-Gln(A)-Met-Glu(C)-OZ, wherein each Z is independently H or a group which activate electrophilically carboxyl groups selected from Bt, Su, Pfp, Tcp, and Pnp.

15. A process for the production of exenatide comprising:
condensing of one fragment of the claim 13 with one fragment of claim 14 to form the partially or resin-bound protected exenatide sequence;
deprotecting or cleaving from the resin; and
deprotecting, chromatographic purification and lyophilization of exenatide.

16. A partially protected peptide resin conjugate of the formula E-Lys(E)-Cys(B)-Asn(A)-Thr(C)-Y-Cys(B)-Y-Gln(A)-Arg(D)-Leu-Ala-Asn(A)-Phe-Leu-Val-His(A)-X-Asn(A)-Asn(A)-Phe-Gly-Pro-Ile-Leu-Pro-Pro-Thr(C)-Asn(A)-Val-Gly- Ser(C)-Asn(A)-Thr(C)-Tyr(Resin)-NH$_2$ wherein X=Ser(tBu)-Ser(tBu) or Ser(tBu)-ψSer, wherein:
Y is Ala-Thr(tBu) or Ala-ψThr;
each A is independently H, a carboxamido or imidazol protecting group selected from Trt, Mtt, and Mmt;
each B is independently a Cys protecting group selected from Mmt, Trt, Acm, and StBu;
each C is independently hydroxyl, carboxy or phenoxy protecting group selected from tBu, Trt, and 2-chlorotrityl (Clt);
D is H or a guanidine protecting group selected from Pbf and Pmc;
E is H or an amino protecting group selected from Fmoc, Boc, Trt, Nps, Mtt, Mmt, and 2-chlorotrityl (Clt); and
Resin is H or an acid labile resin suitable for solid-phase peptide synthesis.

17. A protected or partially protected peptide resin conjugate with the sequence Z-Asn(A)-Phe-Leu-Val-His(A)-X-Asn(A)-Asn(A)-Phe-Gly-Pro-Ile-Leu-Pro-Pro-Thr(C)-Asn(A)-Val-Gly-Ser(C)-Asn(A)-Thr(C)-Tyr(Resin)-NH$_2$ in particular the protected or partially protected 10-38, 11-38, 12-38 and 14-38 partially protected pramlintide fragments wherein:
Z is H or E-Gln(A)-Arg(D)-Leu-Ala, E-Arg(D)-Leu-Ala, E-Leu-Ala or E-Ala;

X is Ser(tBu)-Ser(tBu) or Ser(tBu)-ψSer;
A is H or a carboxamido or imidazol protecting group selected from Trt, Mtt, and Mmt;
C is a hydroxyl, carboxy or phenoxy protecting group selected from tBu, Trt, and 2-chlorotrityl (Clt);
D is H or a guanidine protecting group selected from Pbf and Pmc;
E is H or an amino protecting group selected from Fmoc, Boc, Trt, Nps, Mtt, Mmt, and 2-chlorotrityl (Clt); and
Resin is H or an acid labile resin suitable for solid-phase peptide synthesis.

18. A process for the preparation of partially protected and oxidized pramlintide fragments of formulae I, II, III, or IV:

$$\text{E-Lys(E)-Cys-Asn(A)-Thr(C)-Y-Cys-Y-Gln(A)-Arg(D)-Leu-Ala-OZ;} \quad (I)$$

$$\text{E-Lys(E)-Cys-Asn(A)-Thr(C)-Y-Cys-Y-Gln(A)-Arg(D)-OZ;} \quad (II)$$

$$\text{E-Lys(E)-Cys-Asn(A)-Thr(C)-Y-Cys-Y-Gln(A)-OZ;} \quad (III)$$

$$\text{E-Lys(E)-Cys-Asn(A)-Thr(C)-Y-Cys-Y-OZ;} \quad (IV)$$

wherein:
each Y is independently Ala-Thr(tBu) or Ala-ψThr;
Z is H or a group selected from Bt, Su, Pfp, Tcp, and Pnp;
each A is independently H or a carboxamido or imidazol protecting group selected from Trt, Mtt, and Mmt;
each C is independently a hydroxy, carboxyl or phenoxy protecting group selected from tBu, Trt, or 2-chlorotrityl (Clt);
each D is independently H or a guanidine protecting group selected from Pbf and Pmc;
each E is independently H or an amino protecting group selected from Fmoc, Boc, Trt, Nps, Mtt, Mmt, or 2-chlorotrityl (Clt);
said process comprising:
assembling protected peptides on an acid sensitive resin, such as a 2-CTC-resin;
cleaving the protected peptide from the resin; and
oxidizing the resin-bound peptides by contacting the resin-bound peptides with mild acid, such as dilute trifluoroacetic acid in an organic solvent, such as dichloromethane, wherein the solvent comprises a 2-200 molar excess of iodine over the fragment.

19. A process for the production of pramlintide, where a fragment of claim 18 is condensed in solution or on solid phase with one of the fragments of claim 17, claim 18 or one of the fragments of the formula E-Lys(E)-Cys(B)-Asn(A)-Thr(C)-Y-Cys(B)-Y-Gln(A)-Arg(D)-Leu-Ala-OZ, E-Lys(E)-Cys(B)-Asn(A)-Thr(C)-Y-Cys(B)-Y-Gln(A)-Arg(D)-OZ, E-Lys(E)-Cys(B)-Asn(A)-Thr(C)-Y-Cys(B)-Y-Gln(A)-OZ, E- Lys(E)-Cys(B)-Asn(A)-Thr(C)-Y-Cys(B)-Y-OZ, wherein:
each Y is independently Ala-Thr(tBu) or Ala-ψThr;
Z is H or a group selected from Bt, Su, Pfp, Tcp, and Pnp;
each A is independently H or a carboxamido or imidazol protecting group selected from Trt, Mtt, and Mmt;
each C is independently a hydroxy, carboxyl or phenoxy protecting group selected from tBu, Trt, and 2-chlorotrityl (Clt);
each D is independently H or a guanidine protecting group selected from Pbf and Pmc;
each E is independently H or an amino protecting group selected from Fmoc, Boc, Trt, Nps, Mtt, Mmt, and 2-chlorotrityl (Clt);
each B is independently a Cys protecting group selected from Mmt, Trt, Acm, and StBu and
Resin is H or an acid labile resin suitable for solid-phase peptide synthesis.

20. A process for the preparation of bivalirudin comprising:
condensing a bivalirudin peptide resin conjugate fragment of the formula:

$$\text{E-X-Tyr(Resin)-Leu-O-C;}$$

wherein:
X is an 11-18 partially protected bivalirudin fragment;
E is H or an amino protecting group selected from Fmoc, Boc, Trt, Nps, Mtt, Mmt, and 2-chlorotrityl (Clt);
C is a hydroxyl carboxyl protecting group selected from tBu, Trt, and 2-chlorotrityl (Clt); and
Resin is H or an acid labile resin suitable for solid-phase peptide synthesis;
in solution or on solid phase with a bivalirudin peptide resin conjugate fragment of the formula:

$$\text{E-D-Phe-Y-OZ;}$$

wherein:
Y is a 2-10 partially protected bivalirudin fragment;
Z is H or a group selected from Bt, Su, Pfp, Tcp, and Pnp; and
D-designates the chirality of the amino acid that follows as being a D-amino acid; to give:

$$\text{E-D-Phe-Y-X-Tyr(Resin)-Leu-O-C;}$$

wherein the method further comprises:
deprotecting, or cleaving from the resin and deprotecting to provide bivalirudin;
of purifying the bivalirudin by chromatography; and
lyophilizing the bivalirudin to provide bivalirudin in >99% purity.

21. A protected or partially protected peptide resin conjugate with the formula E-Ser(C)-Tyr(C)-Ser(C)-Met-Glu(C)-His(A)-Phe-Arg(D)-Trp(F)-Gly-Lys(E)-Pro-Val-Gly-Lys(E)-Lys(E)-Arg(D)-Arg(D)-Pro-Val-Lys(E)-Val-Tyr(Resin)-Pro-O-C, wherein:
A is H or a carboxamido or imidazol protecting group selected from Trt, Mtt, and Mmt;
each C is independently a hydroxy, carboxyl or phenoxy protecting group selected from tBu, Trt, and 2-chlorotrityl (Clt);
each D is independently H or a guanidine protecting group selected from Pbf and Pmc;
each E is independently H or an amino protecting group selected from Fmoc, Boc, Trt, Nps, Mtt, Mmt, and 2-chlorotrityl (Clt);
F is H or Boc and
Resin is H or an acid labile resin suitable for solid-phase peptide synthesis.

22. A protected or partially protected fragment with the formula E-X-Tyr(Resin)-Pro-O-C wherein:
X is a ACTH(1-24) sequence;
E is H or an amino protecting group selected from Fmoc, Boc, Trt, Nps, Mtt, Mmt, and 2-chlorotrityl (Clt);
C is a hydroxy, carboxyl or phenoxy protecting group selected from tBu, Trt, and 2-chlorotrityl (Clt); and Resin is H or an acid labile resin suitable for solid-phase peptide synthesis.

23. A process for the production of ACTH(1-24) comprising:

condensing a ACTH peptide resin conjugate fragment of the formula E-X-Tyr(Resin)-Pro-O-C of claim 22 in solution or in solid phase with a ACTH fragment of the formula E-Y-OZ to give E-Y-X-Tyr(Resin)-Pro-O-C;

deprotecting or cleaving from the resin and deprotection provides ACTH(1-24) which is purified by chromatography and lyophilized to provide ACTH(1-24) of >99% purity, wherein;

X and Y are each independently ACTH sequences;

C is a hydroxy protecting group selected from 2-chlorotrityl Trt, and tBu;

E is an amino protecting group selected from Fmoc, Mtt, Mmt, Trt, Boc, and Nps; and Resin represents H or an acid labile resin suitable for solid-phase peptide synthesis.

24. A process according to claim 20 which comprises condensation of the peptide resin conjugate bivalirudin fragment (11-20):

H-Asp(tBu)-Phe-Glu(tBu)-Glu(tBu)-Ile-Pro-Glu(tBu)-Glu(tBu)-Tyr(Resin)-Leu-O-tBu, with a protected peptide bivalirudin fragment (1-10) of formula:

Boc-D-Phe-Pro-Arg(pbf)-Pro-Gly-Gly-Gly-Gly-Asn(Trt)-Gly-OH.

* * * * *

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Synthetic polypeptide: Lanreotide
<220> FEATURE:
<221> NAME/KEY: misc_feature
<222> LOCATION: (1)..(1)
<223> OTHER INFORMATION: Xaa = D-2-Naphthyl alanine
<220> FEATURE:
<221> NAME/KEY: misc_feature
<222> LOCATION: (2)..(7)
<223> OTHER INFORMATION: Disulfide bond between Cys(2) and Cys(7)
<220> FEATURE:
<221> NAME/KEY: misc_feature
<222> LOCATION: (4)..(4)
<223> OTHER INFORMATION: Xaa = D-Trp

<400> SEQUENCE: 1

Xaa Cys Tyr Xaa Lys Val Cys Thr
1               5

<210> SEQ ID NO 2
<211> LENGTH: 30
<212> TYPE: PRT
<213> ORGANISM: human
<220> FEATURE:
<221> NAME/KEY: misc_feature
<223> OTHER INFORMATION: human insulin B-chain

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 8
<212> TYPE: PRT
<213> ORGANISM: human
<220> FEATURE:
<221> NAME/KEY: misc_feature
```

-continued

```
<222> LOCATION: (1)..(8)
<223> OTHER INFORMATION: human insulin B-chain

<400> SEQUENCE: 3

Phe Val Asn Gln His Leu Cys Gly
1               5

<210> SEQ ID NO 4
<211> LENGTH: 22
<212> TYPE: PRT
<213> ORGANISM: human
<220> FEATURE:
<221> NAME/KEY: misc_feature
<223> OTHER INFORMATION: human insulin B-chain

<400> SEQUENCE: 4

Ser His Leu Val Glu Ala Leu Tyr Leu Val Cys Gly Glu Arg Gly Phe
1               5                   10                  15

Phe Tyr Thr Pro Lys Thr
            20

<210> SEQ ID NO 5
<211> LENGTH: 32
<212> TYPE: PRT
<213> ORGANISM: salmon
<220> FEATURE:
<221> NAME/KEY: misc_feature
<223> OTHER INFORMATION: salmon calcitonin
<220> FEATURE:
<221> NAME/KEY: misc_feature
<222> LOCATION: (1)..(7)
<223> OTHER INFORMATION: Disulfide bond between Cys 1 and Cys 7
<220> FEATURE:
<221> NAME/KEY: misc_feature
<222> LOCATION: (32)..(32)
<223> OTHER INFORMATION: Pro-amide

<400> SEQUENCE: 5

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 6
<211> LENGTH: 10
<212> TYPE: PRT
<213> ORGANISM: salmon
<220> FEATURE:
<221> NAME/KEY: misc_feature
<222> LOCATION: (1)..(10)
<223> OTHER INFORMATION: salmon calcitonin
<220> FEATURE:
<221> NAME/KEY: misc_feature
<222> LOCATION: (1)..(7)
<223> OTHER INFORMATION: Disulfide bond between Cys 1 and Cys 7

<400> SEQUENCE: 6

Cys Ser Asn Leu Ser Thr Cys Val Leu Gly
1               5                   10

<210> SEQ ID NO 7
<211> LENGTH: 22
<212> TYPE: PRT
<213> ORGANISM: salmon
<220> FEATURE:
<221> NAME/KEY: misc_feature
<223> OTHER INFORMATION: salmon calcitonin
<220> FEATURE:
<221> NAME/KEY: misc_feature
```

```
<222> LOCATION: (22)..(22)
<223> OTHER INFORMATION: Pro-amide

<400> SEQUENCE: 7

Lys Leu Ser Gln Glu Leu His Lys Leu Gln Thr Tyr Pro Arg Thr Asn
1               5                   10                  15

Thr Gly Ser Gly Thr Pro
            20

<210> SEQ ID NO 8
<211> LENGTH: 8
<212> TYPE: PRT
<213> ORGANISM: Artificial sequence
<220> FEATURE:
<223> OTHER INFORMATION: Synthetic peptide: octreotide
<220> FEATURE:
<221> NAME/KEY: misc_feature
<222> LOCATION: (1)..(1)
<223> OTHER INFORMATION: Xaa = D-Phe
<220> FEATURE:
<221> NAME/KEY: misc_feature
<222> LOCATION: (2)..(7)
<223> OTHER INFORMATION: Disulfide bond between Cys 2 and Cys 7
<220> FEATURE:
<221> NAME/KEY: misc_feature
<222> LOCATION: (4)..(4)
<223> OTHER INFORMATION: Xaa = D-Trp
<220> FEATURE:
<221> NAME/KEY: misc_feature
<222> LOCATION: (8)..(8)
<223> OTHER INFORMATION: Xaa = L-threoninol

<400> SEQUENCE: 8

Xaa Cys Phe Xaa Lys Thr Cys Xaa
1               5

<210> SEQ ID NO 9
<211> LENGTH: 39
<212> TYPE: PRT
<213> ORGANISM: Gila monster
<220> FEATURE:
<221> NAME/KEY: misc_feature
<223> OTHER INFORMATION: Exenatide; Synonyms: exendin 4, byetta
<220> FEATURE:
<221> NAME/KEY: misc_feature
<222> LOCATION: (39)..(39)
<223> OTHER INFORMATION: Ser-amide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
            35

<210> SEQ ID NO 10
<211> LENGTH: 11
<212> TYPE: PRT
<213> ORGANISM: Artificial sequence
<220> FEATURE:
<223> OTHER INFORMATION: Synthetic peptide: exenatide fragment 1-11

<400> SEQUENCE: 10

His Gly Glu Gly Thr Phe Thr Ser Asp Leu Ser
1               5                   10

<210> SEQ ID NO 11
```

```
<211> LENGTH: 28
<212> TYPE: PRT
<213> ORGANISM: Artificial sequence
<220> FEATURE:
<223> OTHER INFORMATION: Synthetic polypeptide: exenatide fragment 12-39
<220> FEATURE:
<221> NAME/KEY: misc_feature
<222> LOCATION: (28)..(28)
<223> OTHER INFORMATION: Ser-amide

<400> SEQUENCE: 11

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 12
<211> LENGTH: 13
<212> TYPE: PRT
<213> ORGANISM: Artificial sequence
<220> FEATURE:
<223> OTHER INFORMATION: Synthetic peptide: exenatide fragment 1-13

<400> SEQUENCE: 12

His Gly Glu Gly Thr Phe Thr Ser Asp Leu Ser Lys Gln
1               5                   10

<210> SEQ ID NO 13
<211> LENGTH: 26
<212> TYPE: PRT
<213> ORGANISM: Artificial sequence
<220> FEATURE:
<223> OTHER INFORMATION: Synthetic peptide: exenatide fragment 14-39
<220> FEATURE:
<221> NAME/KEY: misc_feature
<222> LOCATION: (26)..(26)
<223> OTHER INFORMATION: Ser-amide

<400> SEQUENCE: 13

Met Glu Glu Glu Ala Val Arg Leu Phe Ile Glu Trp Leu Lys Asn Gly
1               5                   10                  15

Gly Pro Ser Ser Gly Ala Pro Pro Pro Ser
            20                  25

<210> SEQ ID NO 14
<211> LENGTH: 24
<212> TYPE: PRT
<213> ORGANISM: human
<220> FEATURE:
<221> NAME/KEY: misc_feature
<223> OTHER INFORMATION: ACTH 1-24; Synonyms: Tetracosactide, Synacthen

<400> SEQUENCE: 14

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 15
<211> LENGTH: 10
<212> TYPE: PRT
<213> ORGANISM: human
<220> FEATURE:
<221> NAME/KEY: misc_feature
<223> OTHER INFORMATION: ACTH 1-24

<400> SEQUENCE: 15
```

```
Ser Tyr Ser Met Glu His Phe Arg Trp Gly
1               5                   10

<210> SEQ ID NO 16
<211> LENGTH: 14
<212> TYPE: PRT
<213> ORGANISM: human
<220> FEATURE:
<221> NAME/KEY: misc_feature
<223> OTHER INFORMATION: ACTH 11-24

<400> SEQUENCE: 16

Lys Pro Val Gly Lys Lys Arg Arg Pro Val Lys Val Tyr Pro
1               5                   10

<210> SEQ ID NO 17
<211> LENGTH: 37
<212> TYPE: PRT
<213> ORGANISM: Artificial Sequence
<220> FEATURE:
<223> OTHER INFORMATION: Synthetic polypeptide, symlin. Synonyms:
      Pramlintide; amylin analogue

<400> SEQUENCE: 17

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide: Pramlintide 1-10

<400> SEQUENCE: 18

Lys Cys Asn Thr Ala Thr Cys Ala Thr Gln
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide: Pramlintide 1-11

<400> SEQUENCE: 19

Lys Cys Asn Thr Ala Thr Cys Ala Thr Gln
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide: Pramlintide 1-12

<400> SEQUENCE: 20

Lys Cys Asn Thr Ala Thr Cys Ala Thr Gln
1               5                   10

<210> SEQ ID NO 21
<211> LENGTH: 10
```

```
<212> TYPE: PRT
<213> ORGANISM: Artificial Sequence
<220> FEATURE:
<223> OTHER INFORMATION: Synthetic peptide: Pramlintide 1-14

<400> SEQUENCE: 21

Lys Cys Asn Thr Ala Thr Cys Ala Thr Gln
1               5                   10

<210> SEQ ID NO 22
<211> LENGTH: 27
<212> TYPE: PRT
<213> ORGANISM: Artificial Sequence
<220> FEATURE:
<223> OTHER INFORMATION: Synthetic peptide: Pramlintide 11-38

<400> SEQUENCE: 22

Arg Leu Ala Asn Phe Leu Val His Ser Ser Asn Asn Phe Gly Pro Ile
1               5                   10                  15

Leu Pro Pro Thr Asn Val Gly Ser Asn Thr Tyr
            20                  25

<210> SEQ ID NO 23
<211> LENGTH: 26
<212> TYPE: PRT
<213> ORGANISM: Artificial Sequence
<220> FEATURE:
<223> OTHER INFORMATION: Synthetic peptide: Pramlintide 12-38

<400> SEQUENCE: 23

Leu Ala Asn Phe Leu Val His Ser Ser Asn Asn Phe Gly Pro Ile Leu
1               5                   10                  15

Pro Pro Thr Asn Val Gly Ser Asn Thr Tyr
            20                  25

<210> SEQ ID NO 24
<211> LENGTH: 24
<212> TYPE: PRT
<213> ORGANISM: Artificial Sequence
<220> FEATURE:
<223> OTHER INFORMATION: Synthetic peptide: Pramlintide 14-38

<400> SEQUENCE: 24

Asn Phe Leu Val His Ser Ser Asn Asn Phe Gly Pro Ile Leu Pro Pro
1               5                   10                  15

Thr Asn Val Gly Ser Asn Thr Tyr
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptide: Bivalirudin, Synonyms:
      Angiox, Angiomax. Blood dilutant
<220> FEATURE:
<221> NAME/KEY: misc_feature
<222> LOCATION: (1)..(1)
<223> OTHER INFORMATION: Xaa = D-Leu

<400> SEQUENCE: 25

Xaa Pro Arg Pro Gly Gly Gly Gly Asn Gly Asp Phe Glu Glu Ile Pro
1               5                   10                  15

Glu Glu Tyr Leu
            20
```

```
<210> SEQ ID NO 26
<211> LENGTH: 10
<212> TYPE: PRT
<213> ORGANISM: Artificial Sequence
<220> FEATURE:
<223> OTHER INFORMATION: Synthetic peptide: Bivalirudin
<220> FEATURE:
<221> NAME/KEY: misc_feature
<223> OTHER INFORMATION: Synonyms: Angiox, Angiomax. Blood dilutant
<220> FEATURE:
<221> NAME/KEY: misc_feature
<222> LOCATION: (1)..(1)
<223> OTHER INFORMATION: Xaa = D-Leu

<400> SEQUENCE: 26

Xaa Pro Arg Pro Gly Gly Gly Gly Asn Gly
1               5                   10
```